United States Patent
Kadel et al.

(10) Patent No.: US 7,645,383 B2
(45) Date of Patent: *Jan. 12, 2010

(54) MICROSTRUCTURED FILTER

(75) Inventors: Klaus Kadel, Willen (DE); Johannes Geser, Dortmund (DE); Joachim Eicher, Dortmund (DE); Bernhard Freund, Gau-Algesheim (DE); Stephen Terence Dunne, Suffolk (GB); Wulf Bachtler, Mainz (DE)

(73) Assignee: Boehringer Ingelheim International GmbH, Ingelheim (DE)

(*) Notice: Subject to any disclaimer, the term of this patent is extended or adjusted under 35 U.S.C. 154(b) by 34 days.

This patent is subject to a terminal disclaimer.

(21) Appl. No.: 11/249,268

(22) Filed: Oct. 14, 2005

(65) Prior Publication Data

US 2006/0032494 A1    Feb. 16, 2006

Related U.S. Application Data

(63) Continuation of application No. 10/780,864, filed on Feb. 19, 2004, now Pat. No. 6,977,042, which is a continuation of application No. 09/509,201, filed as application No. PCT/GB98/02604 on Aug. 28, 1998, now Pat. No. 6,846,413.

(30) Foreign Application Priority Data

Sep. 26, 1997   (DE) ................. 197 42 439

(51) Int. Cl.
  *B01D 63/00* (2006.01)
  *A61M 11/00* (2006.01)

(52) U.S. Cl. ............... 210/321.86; 210/493.1; 210/500.26; 216/56; 128/200.14

(58) Field of Classification Search ............. 210/314, 210/321.84, 321.86, 336, 348, 483, 488, 210/490, 493.1, 493.5, 498, 500.22, 500.26; 128/200.14; 216/2, 56

See application file for complete search history.

(56) References Cited

U.S. PATENT DOCUMENTS 3,347,473 A   10/1967   Steck (Continued)

FOREIGN PATENT DOCUMENTS

CA        2245566        8/1997

(Continued)

OTHER PUBLICATIONS

Angell, James B., Terry, Stephen C. and Barth, Phillip W., *Silicon Micromechanical Devices*, Sci. Am. 248:(4)36-47 Apr. 1983.

(Continued)

*Primary Examiner*—John Kim
(74) *Attorney, Agent, or Firm*—Michael P. Morris; Mary-Ellen M. Devlin; David L. Kershner

(57) ABSTRACT

A microstructured filter is presented having an inlet for unfiltered fluid; an outlet for filtered fluid; a plurality of projections, which form at least one row in a mutually juxtaposed relationship across the filter, that project out of a base plate and are an integral component of the base plate; a plurality of passages between the projections; and a cover plate which is securable to the base plate to cover the projections and the passages. The passages form a plurality of through paths from the inlet to the outlet. The inlet includes an elongate inlet slot for the unfiltered fluid that extends over approximately the entire filter width and is approximately as high as the projection on the outlet side of the filter.

20 Claims, 3 Drawing Sheets

U.S. PATENT DOCUMENTS

| | | | |
|---|---|---|---|
| 3,397,278 A | 8/1968 | Pomerantz | |
| 3,615,054 A | 10/1971 | La Botz | |
| 3,771,724 A | 11/1973 | Rose et al. | |
| 3,921,916 A | 11/1975 | Bassous | |
| 3,948,777 A | 4/1976 | Murata et al. | |
| 3,965,012 A | 6/1976 | Eguchi et al. | |
| 4,151,955 A | 5/1979 | Stouffer | |
| 4,334,992 A | 6/1982 | Von Bonin et al. | |
| 4,601,921 A | 7/1986 | Lee | |
| 4,681,258 A | 7/1987 | Jenkins et al. | |
| 4,688,056 A | 8/1987 | Noguchi et al. | |
| 4,797,211 A * | 1/1989 | Ehrfeld et al. | 210/321.84 |
| 4,828,184 A | 5/1989 | Gardner et al. | |
| 4,829,324 A | 5/1989 | Drake et al. | |
| 4,875,968 A | 10/1989 | O'Neill et al. | |
| 4,899,937 A | 2/1990 | Haruch | |
| 4,915,718 A | 4/1990 | Desai | |
| 4,936,954 A | 6/1990 | Sander | |
| 5,084,178 A | 1/1992 | Miller et al. | |
| 5,160,403 A | 11/1992 | Fisher et al. | |
| 5,215,655 A | 6/1993 | Mattermaier | |
| 5,320,096 A | 6/1994 | Hans | |
| 5,332,466 A | 7/1994 | Nozawa | |
| 5,334,247 A | 8/1994 | Columbus et al. | |
| 5,401,403 A | 3/1995 | Hagqvist | |
| 5,460,720 A | 10/1995 | Schneider | |
| 5,472,143 A | 12/1995 | Bartels et al. | |
| 5,487,378 A | 1/1996 | Robertson et al. | |
| 5,547,094 A * | 8/1996 | Bartels et al. | 216/33 |
| 5,587,128 A | 12/1996 | Wilding et al. | |
| 5,759,014 A | 6/1998 | Van Lintel | |
| 5,762,789 A | 6/1998 | De los Reyes et al. | |
| 5,770,076 A | 6/1998 | Chu et al. | |
| 5,782,791 A | 7/1998 | Peterson et al. | |
| 5,814,219 A | 9/1998 | Friedmann et al. | |
| 5,820,767 A | 10/1998 | Kane et al. | |
| 5,855,801 A | 1/1999 | Lin et al. | |
| 5,871,645 A | 2/1999 | Reed et al. | |
| 5,902,365 A | 5/1999 | Haggard | |
| 5,904,846 A | 5/1999 | Clements et al. | |
| 5,980,759 A | 11/1999 | Proulx et al. | |
| 5,985,142 A | 11/1999 | Belden | |
| 5,988,400 A | 11/1999 | Karachevtcev et al. | |
| 5,997,263 A * | 12/1999 | Van Lintel et al. | 417/413.2 |
| 6,000,558 A | 12/1999 | Proulx et al. | |
| 6,010,458 A | 1/2000 | Roberts | |
| 6,103,119 A | 8/2000 | Clements et al. | |
| 6,110,368 A | 8/2000 | Hopkins et al. | |
| 6,113,784 A | 9/2000 | Stoyell et al. | |
| 6,732,868 B2 | 5/2004 | Takagaki et al. | |
| 6,846,413 B1 | 1/2005 | Kadel et al. | |
| 6,977,042 B2 | 12/2005 | Kadel et al. | |
| 2003/0121845 A1 | 7/2003 | Wagner et al. | |

FOREIGN PATENT DOCUMENTS

| | | |
|---|---|---|
| CL | 30360 | 6/1977 |
| CL | 37919 | 5/1991 |
| CL | 230-97 | 2/1996 |
| DE | 916 879 | 8/1954 |
| EP | 0 041 729 | 12/1981 |
| EP | 0 231 432 A2 | 8/1987 |
| EP | 0 231 432 A3 | 8/1987 |
| EP | 0 255 208 B1 | 2/1988 |
| EP | 0 397 441 | 11/1990 |
| EP | 0587912 | 3/1994 |
| GB | 1515892 | 6/1978 |
| GB | 2065505 | 7/1981 |
| GB | 2248891 | 4/1992 |
| JP | 50-29166 | 3/1975 |
| JP | 50-29165 | 9/1975 |
| JP | 53-7819 | 1/1978 |
| JP | 56-113367 | 9/1981 |
| JP | 57-182452 | 11/1982 |
| JP | 2-229050 | 9/1990 |
| JP | 3-267173 | 11/1991 |
| WO | WO 79/00236 | 5/1979 |
| WO | WO 91/14468 | 10/1991 |
| WO | WO 92/10301 | 6/1992 |
| WO | WO 92/10306 | 6/1992 |
| WO | WO 92/19383 | 11/1992 |
| WO | WO 93/11862 | 6/1993 |
| WO | WO 95/19502 | 7/1995 |
| WO | WO 97/12687 | 4/1997 |
| WO | WO 97/29283 * | 8/1997 |

OTHER PUBLICATIONS

Peterson, Kurt, *Silicon as a Mechanical Material*, *Proceedings of the IEEE* 70(5):420-456 May 1982.

* cited by examiner

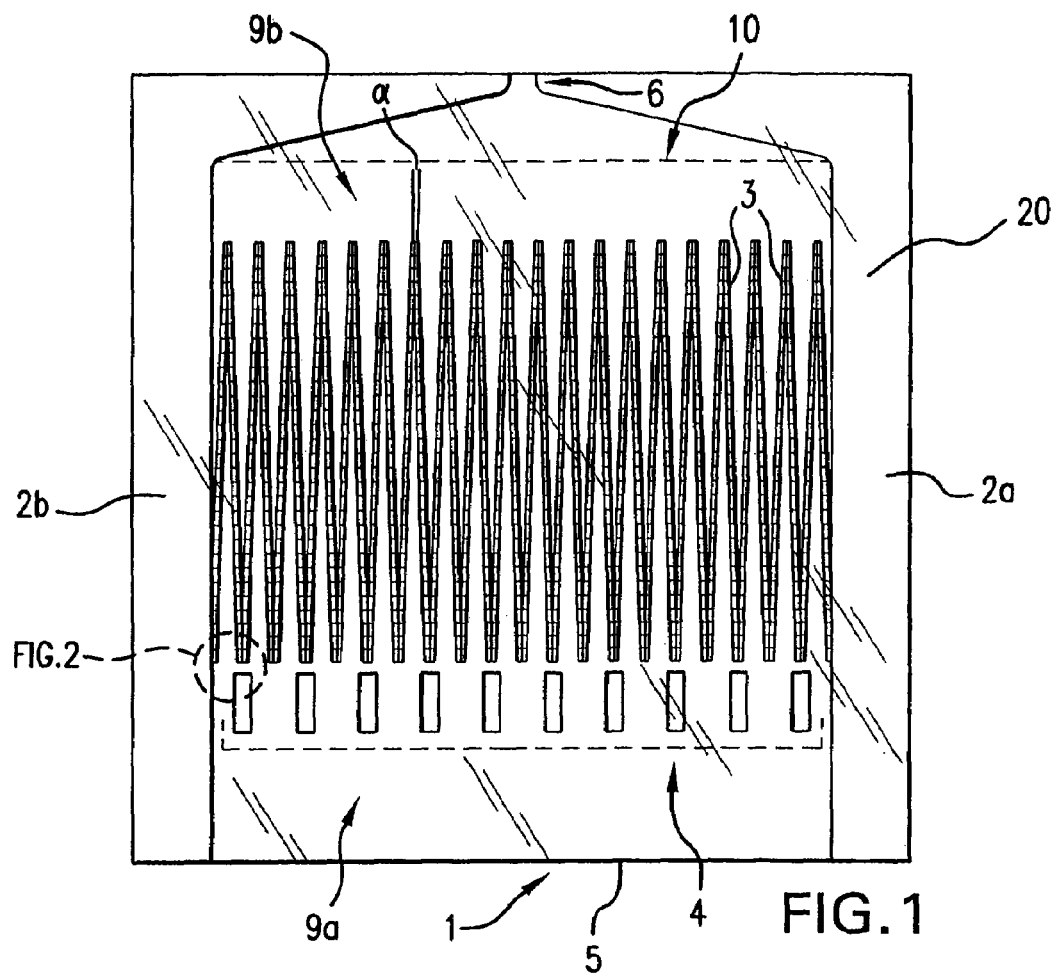
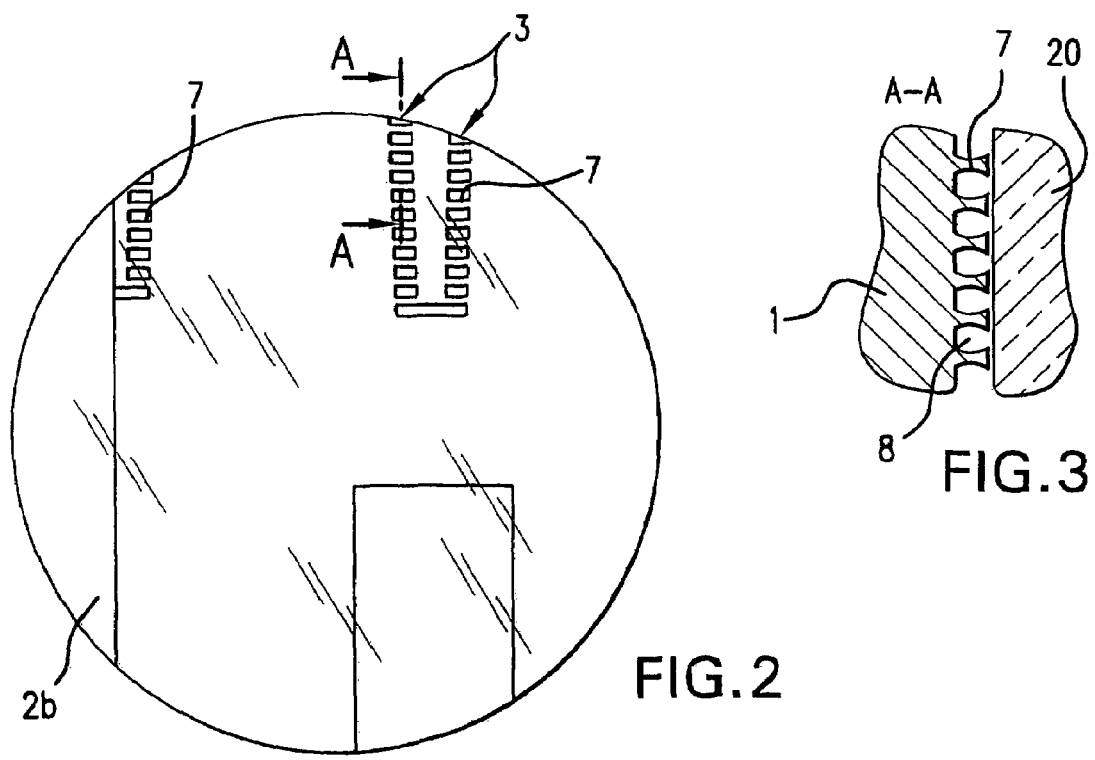
FIG.1
FIG.2
FIG.3

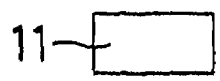 11
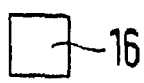 16
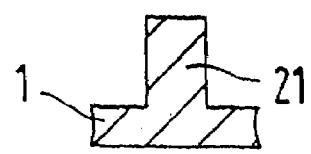 21
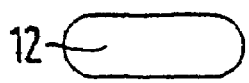 12
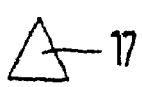 17
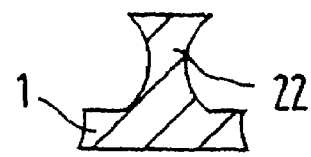 22
 13
 18
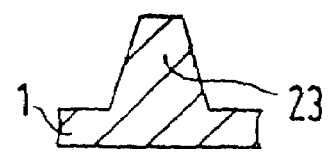 23
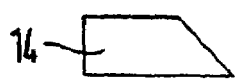 14
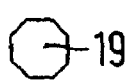 19
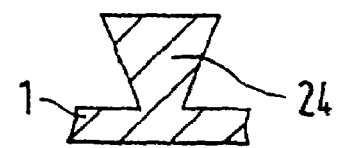 24
 15
 25
FIG.4          FIG.5
 31     35
 32     
 33     36
 34     
FIG.6

MICROSTRUCTURED FILTER

CROSS-REFERENCE TO RELATED APPLICATIONS

The present application is a continuation of U.S. application Ser. No. 10/780,864, filed Feb. 19, 2004, issued as U.S. Pat. No. 6,977,042, which is a continuation of U.S. application Ser. No. 09/509,201, having a 35 U.S.C. § 371 date of Jun. 15, 2000, issued as U.S. Pat. No. 6,846,413, which was a National Phase application based on International Application No. PCT/GB98/02604, filed Aug. 28, 1998. The present application also claims the benefit under 35 U.S.C. § 119 of German patent application DE 197 42 439.2, having a filing date of Sep. 26, 1997. The disclosure of these referenced applications are incorporated by reference herein in their entirety.

BACKGROUND OF THE INVENTION

1. Field of the Invention

This invention relates to microstructured filters for fluids.

2. Background of the Invention

Various filters are known, in which the filter medium has micropores down into the submicrometer range, the pore size being statistically distributed in dependence on the material. The external dimensions of filter media of this kind are powers of ten greater than the mean pore diameter and experience has shown that they cannot readily be made as small as may be desired.

Micro-apertured metal strips which are used for screen printing are also known, up to a thickness of 100 µm, comprising for example nickel, provided with holes which are uniformly distributed over the strip, the diameter of the holes being some micrometers. These strips are produced for example galvanically. Metal strips of this kind cannot be assembled with microstructured components.

European Patent Specification No. 0 231 432 describes a cross-flow microfilter to which the fluid to be filtered is fed and out of which a concentrate flow and a filtrate flow are taken. Disposed between the chamber into which the fluid flows and the collecting chamber for the filtrate is a row of webs or lands between which there are passages. The row of webs and passages forms the microfilter. The direction of the passages is inclined through an angle of 90° to 135° with respect to the direction of flow of the fluid/concentrate. The supplied fluid which goes into the concentrate flows past the row of webs. The filtrate is collected in a plurality of chambers and leaves the filter either perpendicularly to the filter surface or in the filter surface in a plurality of passages which extend between the passages for the concentrate.

International Patent Specification No. WO 93/11862 discloses a micromechanical filter which is constructed from three layers. Disposed on the closed base layer in given regions is an intermediate layer and disposed thereon is a cover layer with openings that are elongate in a region-wise manner. The intermediate layer is missing in parallel relationship to one or both longitudinal sides of the openings. In those regions, the cover layer is arranged in a cantilever or overhung configuration. Disposed under the cantilever part of the cover layer, adjoining the opening, is a shallow slot which is as thick as the intermediate layer and as long as the elongate opening. The filtrate flows through that slot into the filtrate collection chamber which is thicker than the intermediate chamber. The cover layer contains a large number of the elongate openings which are arranged in row-wise manner parallel to each other. The rows of slots can be arranged in a meander configuration in the cover layer. The fluid flows through a plurality of openings perpendicularly to the filter surface into a plurality of inlet chambers and is removed from a plurality of filtrate collecting chambers through a plurality of openings perpendicularly to the filter surface. The layers of that filter can be made from silicon, plastic material or metal and are structured by etching, embossing or mechanical processing or machining, while methods involving thin film technology and metal deposition out of the vapor phase can be included.

These, and other, previously proposed devices suffer from a number of problems. For example, it has been noted that at least some of the previously proposed devices are unduly susceptible to blockage whereupon the device can then cease to function. In an effort to alleviate this problem it has been proposed to provide a larger filter, but these larger filters have an undesirably large dead volume. Also, some of the previously proposed devices are unduly complicated, and thus expensive and time consuming to manufacture. In addition, some of the previously proposed devices are such that they cannot easily be assembled with other microstructured components.

Accordingly it is an object of the invention to provide a microstructured filter for a fluid that alleviates one or more of the problems described herein.

BRIEF SUMMARY OF THE INVENTION

According to an aspect of the invention there is provided a microstructured filter having an inlet for unfiltered fluid and an outlet for filtered fluid, the filter comprising:

a filter chamber provided between said inlet and said outlet, said chamber being partly defined by a substantially flat base plate and a cover plate that is securable thereto; and a filter body provided within the filter chamber, said filter body being formed by plurality of projections that each comprise an integral component of said base plate and which each project therefrom, said projections being spaced from one another by passages that form a a fluid path through the filter chamber from said inlet to said outlet, said cover plate when secured to the base plate covering said projections and said passages;

wherein said plurality of projections are arranged in at least two rows to extend in a zig-zag configuration and in a mutually juxtaposed relationship across the filter chamber; and the inlet and the outlet each comprise an elongate slot for unfiltered and filtered fluid respectively, each of said slots being substantially as wide as the filter chamber and substantially as high as the projections on the inlet and outlet sides of the filter body respectively.

A preferred embodiment of the invention provides a microstructured filter for a fluid having an inlet for the unfiltered fluid and an outlet for the filtered fluid, wherein the flow direction of the fluid through the entire filter is in a surface, having the following characterizing features:

a plurality of projections which are arranged in row-wise manner in mutually juxtaposed relationship and which project out of a preferably flat—base plate and which are an integral component of the base plate, a plurality of passages between the projections, a—preferably flat—cover plate which is disposed over the projections and which covers the passages, wherein the passages form a through path from the inlet side to the outlet side of the filter, and the spacing between the base plate in the area around the projections and the cover plate within a row of projections is approximately as large as the width of the passages on the side of the projections, on which the fluid passes into the row of passages, and an elongate inlet slot for the unfiltered fluid, which extends over approximately the entire width of the filter and which is approximately as high as the projections which project out of the base plate on the inlet side of the filter, and an elongate outlet slot for the filtered fluid, which extends over approximately the entire width of the filter and which is approximately as high as the projections which project out of the base plate, on the outlet side of the filter.

Preferably, the ratio of height to width of the inlet slot and the outlet slot is from 1:5 to 1:1000. The inlet slot preferably retains coarse particles.

A plurality of rows of projections can be arranged in a cascade configuration. The projections arranged closer to the inlet side of the filter are preferably larger than the projections which are arranged more at the outlet side of the filter.

The spacing between the flat base plate and the flat cover plate in the region around each row of projections, which row is arranged in a cascade configuration, is preferably approximately as large as the width of the passages on the side of the projections, on which the fluid passes into the row of passages. The spacing is preferably between half and double the passage width. The spacing preferably decreases from one row to another, as viewed in the direction of flow. The passages may therefore be of an approximately square cross-section on their entry side for the fluid.

The spacing between the flat base plate in the area around the projections and the flat cover plate can be constant within a row of projections. In the case of rows of projections which are arranged in a meander configuration or a zig-zag configuration, the spacing can be larger in the region of the end of the row which is in the proximity of the outlet side of the filter than in the region of the end of the row which is in the proximity of the inlet side of the filter. The spacing preferably approximately linearly increases from one end of the row of projections to the other.

The mutually facing sides of two adjacent rows of projections may define an interconnected chamber into which the fluid flows from all passages between the projections of a first row, and out of which the fluid flows into all passages between the projections of the adjacent row. Disposed upstream of the first row of projections is a collecting chamber of elongate cross-section, into which the unfiltered fluid is passed and out of which the fluid flows into all passages between the projections of the first row. Disposed downstream of the last row of projections is a collecting chamber of elongate cross-section, into which the fluid flows out of all passages of the last row, and out of which the filtered fluid is passed.

The projections can be in the form of webs or lands which—as viewed in the flow direction—are straight or curved. The projections may also be in the form of preferably straight—columns of any cross-section, preferably of round or polygonal cross-section.

The length of the passages extending between webs or lands is preferably at least twice as great as their height on the entry side of the fluid. The cross-section of the passages is preferably approximately square or barrel-shaped or trapezoidal-in the latter case the longer side of the trapezium can be formed by a cover plate. The passages are for example from 5 to 50 µm in length, from 2.5 to 25 µm in height and from 2.5 to 25 µm in width. The width of the passages can become greater towards the exit side.

The spacing between the rows of projections is preferably twice as great as the passage width on the entry side. The rows of projections can extend parallel to each other or in a meander configuration or a zig-zag configuration. The rows arranged in a zig-zag configuration can be inclined relative to each other through an angle of from 2° to 25°.

When the filter has rows of projections which are arranged in a meander or zig-zag configuration, the particles to be filtered out are firstly deposited in the regions on the inlet side of the fluid, which are in the proximity of the outlet side of the filter, the space between the rows of projections on the inlet side progressively increases, beginning in the region of the outlet side of the filter. The filter is only approximately completely obstructed and the filter capacity exhausted when the inlet chamber between each two rows of projections is almost entirely filled with particles to be filtered out.

The degree of separation of the filter is preferably relatively sharply defined because of minor fluctuations in the dimensions of the passages. The filter may not require a feed flow distributor for the fluid to be filtered and a filtrate collecting device for the filtered fluid.

The filter can be produced using known processes from metal, silicon, glass, ceramic or plastic material for example. The base plate can be made from the same material as, or a different material from, the cover plate. The filter is preferably suitable for the high-pressure range, for example up to 30 MPa (300 bar).

In a microstructured filter according to another embodiment of the invention, further microstructured fluidic elements are arranged on the same base plate, for example a nozzle for spraying a fluid or for producing an aerosol, also in the high-pressure range.

The microstructured filter according to the various embodiments of the invention may exhibit some or all of the following advantages:

because the filter has a large number of passages over a small area it can remain operational even if some passages are blocked by impurities contaminating the fluid. This can enable the useability of the filter when it is assembled with a nozzle for use in an atomizer to be improved, as when used in an atomizer for the administration of a medicament, failure of the atomizer within its specified period of use can have fatal consequences for the user;

the passages can be defined within narrow limits in regard to shape. Cross-sectional area and length (in the most preferred embodiment the dimensions of all passages within a filter are the same);

the passage cross-section can be adapted to further conditions, for example to the cross-section of a nozzle which is connected downstream thereof, a large filter surface area can be disposed within a small filter volume;

before the fluid can pass into the passages the flow of fluid may be directed between rows arranged in a meander or zig-zag configuration substantially perpendicularly to the flow in the passages;

the open filter area (sum of the cross-sectional area of all passages) may be at least 50% of the total filter area;

the filter may have a small dead volume; and the filter can be assembled in a simple fashion with other microstructured components.

The microstructured filter described herein finds particular utility when used for filtering a medicament dissolved in a solvent for producing an aerosol for inhalative application. Suitable solvents are for example water or ethanol or mixtures thereof. Suitable medicaments are for example Berotec, Atrovent, Berodual, Salbutamol, Combivent, Oxivent, Ba 679, BEA 2108 and others.

The filter according to the invention can also be used in a nebulizer, such as those described in PCT-application WO91/14468 or PCT/EP96/04351.

The microstructured filter described herein may be produced in the following illustrative way: a plurality of interconnected base plates, for example of the order of magnitude of some thousand, is simultaneously microstructured on a large surface area and connected in one step to a large flat cover plate (batch process). This combined assembly may then be divided into a number of individual pieces.

This mode of manufacture has some specific advantages. On the one hand batch production affords the possibility of producing particularly inexpensive individual parts with a high degree of precision with structure accuracies of a few micrometers down into the submicrometer range, which would be produced only at substantially greater cost in a serial processing procedure, while on the other hand batch production affords a uniform defined quality in respect of all parts, which can be reproducibly achieved under the same process conditions and is unlikely to slowly change, as would be the case for example in serial processing procedures due to tool wear.

In addition, the position and location of the parts in the process are also predetermined by the design and do not have to be adjusted and set by means of expensive sorting and handling mechanisms as is the case with some of the previously proposed arrangements.

The base plate may be produced, for example, by reactive ion etching, galvano-shaping or, in the case of plastic materials, in accordance with the LIGM process by lithography, galvano-shaping and molding. There may be further structuring processes for producing specific passage shapes. Passages of trapezoidal or barrel-shaped cross-section can be produced by specific over-etching or under-etching. Such shapes can be produced both by dry etching and also with wet etching processes. Triangular passage cross-sections can be produced with anisotropically operative etching processes in monocrystalline base plates of silicon. The base plate is preferably structured by isotropic or anisotropic wet or dry etching or a combination of those processes, particularly preferably by anisotropic dry etching.

The microstructured base plate and the projections thereof can be joined to the flat cover plate for example by anodic bonding of silicon and glass, for example an alkali borosilicate glass. In one example, the glass plate is laid on to the microstructured silicon plate and contacted with an electrode. The entire assembly is heated to temperatures of between 200 and 500° C. and a negative voltage of about 1000 V is applied between the silicon plate and the glass plate. Due to that voltage the positively charged alkali ions pass through the glass to the cathode where they are neutralized. Formed in the class at the transition between the glass and the silicon is a negative space charge which provides for electrostatic attraction of the two surfaces, and which in addition by way of oxygen bridge bonds results in a durable chemical bond between the class surface and the silicon surface.

With the above described illustrative process a cover plate of glass is particularly advantageous for quality assurance because of, on the one hand, the quality of the bond connection and, on the other hand, because defects or included particles which result in malfunctioning of the filter can be easily recognized by optical inspection.

After the bonding procedure the assembly may be divided into individual filters, preferably with a high-speed rotary diamond circular saw, with the inlet side and the outlet side of each filter being, exposed if they are not already previously exposed. The severing cut can be positioned with a degree of accuracy to within a few micrometers.

Besides using anodic bonding, the microstructured base plate can be joined to the flat cover plate by means of ultrasonic welding, laser welding, gluing or soldering or any other means apparent to persons skilled in the art.

BRIEF DESCRIPTION OF THE DRAWINGS/FIGURES

Embodiments of the inventions will now be described by way of example only, with reference to the accompanying figures.

FIG. 1 illustrates a schematic representation of an embodiment of the filter.

FIG. 2 is a view on an enlarged scale showing the arrangement of projections in rows of the filter of FIG. 1.

FIG. 3 is a cross-sectional view along the line A-A of FIG. 2.

FIG. 4 is a schematic illustration of a variety of different projections.

FIG. 5 is a schematic illustration of further projections.

FIG. 6 is a schematic illustration of a number of illustrative patterns in which the projections might be arranged.

DETAILED DESCRIPTION OF THE INVENTION

Figure 7:
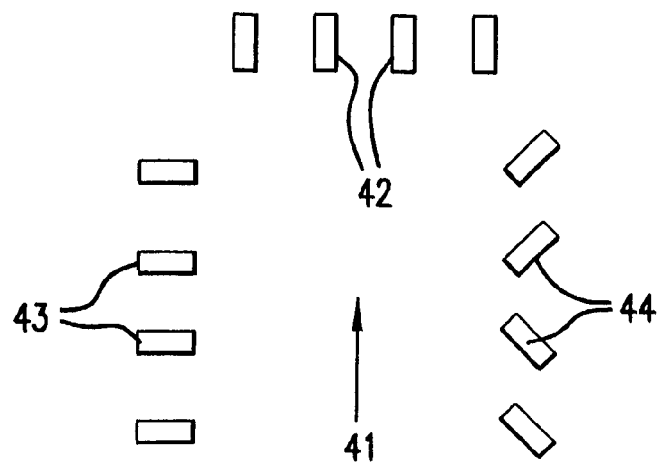
FIG. 7 shows one illustrative example of the orientation of the projections.

As mentioned above, FIG. 1 shows an illustrative embodiment of a filter, viewed from the initially open side, which is then covered with a cover plate 20. A base plate 1 of the filter is microstructured between the edge regions 2*a* and 2*b*. The microstructuring provides, in this example, rows 3 of projections which are arranged in a zig-zag configuration. It may also be seen that the rows 3 are inclined relative to each other through an angle alpha.

In this example, the base plate is provided, in addition to the filter and upstream thereof, with a further row of projections that forms a very coarse filter 4 which serves to agitate the fluid flowing therethrough. Disposed upstream of the further row of projections is an inlet slot 5 through which the unfiltered fluid passes into the filter. In this embodiment, arranged adjoining the filter at an outlet 10 thereof is a nozzle 6 out of which the filtered fluid can exit. The nozzle 6 has been formed, in this illustrative example, as an integral component of the base plate 1. It will be appreciated that the filter can be formed without the nozzle 6 and coarse filter 4.

FIG. 2 is an enlarged view of a portion of FIG. 1 showing an illustrative arrangement of projections in the rows 3. In this case the projections 7 are rectangular webs or lands but, as will be described later, they may have an alternative configuration. It can be seen that the rows 3 comprise a plurality of projections 7 which stand up from the base plate 1 and which are spaced from one another to provide a fine fluid filter.

FIG. 3 is a cross-sectional view through a row of projections taken along line A-A in FIG. 2. In this illustrative embodiment, the projections 7 have concavely curved longitudinal sides, between which there are passages 8 of barrel-shaped cross-section.

FIG. 4 shows a plurality of embodiments of projections, each viewed from the initially open side of the filter (i.e., from above). Any of, or any combination of, the illustrated projections (or any other projection) may be employed in the filter described herein. FIG. 4 shows a rectangular land 11, an elongate land 12 of constant width with rounded narrow sides, a wing-shaped land 13, a land 14 of constant width and with an inclinedly extending narrow side, and a land 15 which is curved in the shape of a segment of a circle. Also illustrated are a square column 16, a triangular column 17, a round column 18 and an octagonal column 19. As mentioned above, any of or any combination of these lands are suitable for use in the filter.

FIG. 5 shows various cross-sectional views through a variety of different projections, more specifically a projection of a rectangular cross-section 21, a projection of a cross-section 22 with concavely curved longitudinal sides, a projection of trapezoidal cross-section 23 in which the long side of the trapezium is connected to the base plate 1, a projection of trapezoidal cross-section 24 in which the short side of the trapezium is connected to the base plate 1, and a projection 25 with two rounded-off longitudinal edges.

FIG. 6 shows various arrangements of projections wherein the projections irrespective of the form thereof—are indicated by dots of different sizes. The projections can be arranged in a matrix form 31 or linearly in a row 32 or in a meander configuration 33 or in a zig-zag configuration 34. A plurality of projections arranged in a row configuration 35 or in a meander or zig-zag configuration 36 can be arranged in succession in cascade relationship.

FIG. 7 shows an illustrative orientation of lands in relation to the intake flow direction 41 of the fluid. As shown, some of the lands (indicated with reference numeral 42) are arranged parallel to the intake flow direction, others of the lands (indicated with reference numeral 43)) are arranged perpendicularly to the intake flow direction and the remainder of the lands (indicated with reference numeral 44) are arranged inclined at different angles to the intake flow direction. It should be understood from FIG. 7 that the lands do not have to have the same orientation with respect to the intake flow direction. In fact, the provision of differently orientated lands is a distinct advantage as the differing orientation serves to improve the degree of fluid agitation as the fluid moves through the filter.

Figure 8:
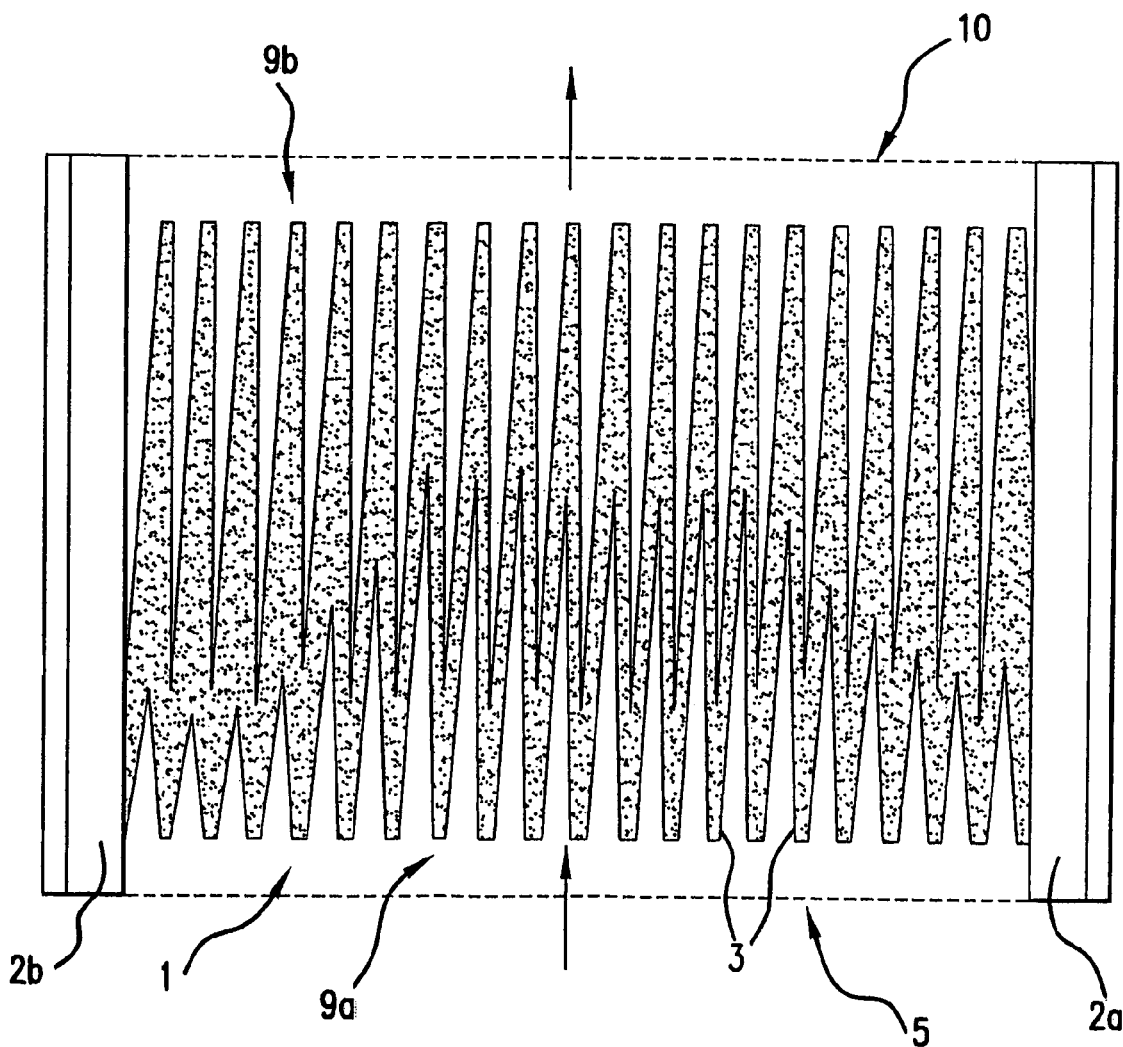
FIG. 8 is an image produced in a scanning electron microscope of a filter at the end of its useful life.

FIG. 8 shows an image produced in a scanning electron microscope of a microstructured filter such as that shown in FIG. 1 at the end of its useful service life. The image was recorded through the cover plate (not visible) of glass. The image shown illustrates a filter having rows of projections arranged in a zia-zag configuration: however the projections themselves cannot be seen at the selected magnification.

Fluid has flowed through the filter in the direction of the arrows during use of the filter, and particles suspended in the fluid have become trapped by adjacent projections. As shown, the rows of projections are covered with filtered-out particles, more specifically to a greater degree in the proximity of the edge regions 2a and 2b than in the central region of the filter. There are almost no particles in the space between the rows of projections, which is at the intake flow side of the filter; and thus the filter is fully operational in that region (i.e., fluid can still pass therethrough). As can be seen from FIG. 8, the limit line between the free filter region and the obstructed filter region extends in an approximately parabolic shape. As seen from FIG. 8, unfiltered fluid entering the inlet slot 5 can still pass through the filter to exit from the outlet slot 10, even though a considerable part of the filter surface area has already been obstructed.

It can be seen therefore that the filter described herein is less prone to blockage than previously proposed filters, as it can still function adequately even when a relatively large proportion of the filter surface has been obstructed. As a result of this improvement, the useful life of the filter (and thus any devices including the filter) may be greatly increased. This is in direct contrast to previously proposed arrangements where a relatively small amount of filter obstruction causes the device to cease functioning correctly.

EXAMPLE

Microstructured Filter for an Atomizer

As mentioned above, the filter described herein finds great utility in atomizers, and in particular in atomizers for producing an aerosol of a medicament-bearing fluid.

An illustrative example of one such atomizer will now be described. In this illustrative example, the filter is formed on a base plate together with a number of other microstuctured components. The base plate is 2.6 mm wide and about 5 mm long. On a width of about 2 mm it contains 40 rows of projections, with the rows arranged in a zig-zag configuration. Each row is 1.33 mm long. The projections are rectangular lands which are 10 μm long and 2.5 μm wide; and they project out of the base plate by 5 μm. Provided between the lands are passages which are 5 μm high and 3 μm wide.

Disposed on the fluid entry side of the filter is a row of 10 rectangular lands which are 200 μm long and 50 μm wide; and they project out of the base plate by 100 μm. Provided between those lands are passages which are 100 μm high and 150 g/m wide. The ten rectangular lands provide a coarse filter and a means for agitating the fluid flowing therethrough. At a spacing of about 300 μm in front of the row of lands there is provided a fluid entry gap which is about 2 mm wide and 100 μm high. With reference to FIG. 1, disposed upstream of the first row of rectangular lands is a collecting chamber 9a of elongate cross-section, into which the unfiltered fluid is passed and out of which the fluid flows into all passages between the lands of the first row.

A filtrate collecting chamber 9b is provided behind the rows of lands arranged in a zig-zag configuration. The filtrate collecting chamber is 5 μm high and gradually narrows from a 2 mm width and which communicates with a nozzle of rectangular cross-section which is 5 μm high and 8 μm wide. In this example, the nozzle opening was produced at the same time as the microstructuring of the base plate.

The base plate which is 1.5 mm thick comprises nickel and is produced by galvano-shaping of a plastic molding insert which contains the complementary structures for 1083 filters. It is covered with a 0.8 mm thick, flat nickel plate which is soldered to the base plate.

What is claimed is:

1. A microstructured filter having an inlet for unfiltered fluid and an outlet for filtered fluid, the filter comprising:
   a substantially flat base plate having a plurality of projections extending therefrom such that each projection is an integral component of the base plate, wherein the projections are spaced from one another by passages that form a fluid path through the filter from the inlet to the outlet;
   a cover plate securable to the base plate for covering the projections and the passages, wherein the plurality of projections form at least one row which is arranged in a meander configuration in a mutually juxtaposed relationship across the filter; and
   wherein the passages have a length of 5 μm to 50 μm, a height of 2.5 μm to 25 μm, and a width of 2.5 μm to 25 μm.

2. The filter according to claim 1, wherein a spacing between the base plate and the cover plate is approximately as large as a width of the passages between adjacent projections.

3. The filter according to claim 1, wherein
the plurality of projections form a plurality of meandering rows of projections arranged in a cascade relationship,
the projections which are arranged closer to the inlet side of the filter are larger than the projections which are arranged more at the outlet side of the filter.

4. The filter according to claim 1, wherein the cover plate is substantially flat.

5. The filter according to claim 1, wherein a spacing between the base plate and the cover plate in the area around the projections within a meandering row of projections is larger in the region of the end of the meandering row which is in the proximity of the outlet side of the filter than in the region of the end of the meandering row which is in the proximity of the inlet side of the filter.

6. The filter according to claim 3, wherein mutually facing sides of two adjacent meandering rows of projections define an interconnected space into which the fluid flows from all passages between the projections of a first row and out of which the fluid flows into all passages between the projections of the row following in the direction of flow.

7. The filter according to claim 1, wherein the projections are in the form of lands which, as viewed in the flow direction, are straight.

8. The filter according to claim 1, wherein the projections are in the form of lands which, as viewed in the flow direction, are curved.

9. The filter according to claim 1, wherein the projections are in the form of lands which, as viewed in the flow direction, are in the form of columns.

10. The filter according to claim 1, wherein the lands are arranged in varying orientations with respect to the flow direction.

11. The filter according to claim 1, wherein the passages are of substantially constant cross-section, and have a length that is at least twice as great as their height on the entry side of the fluid.

12. The filter according to claim 1, wherein the passages are of an approximately constant cross-section over the passage length.

13. The filter according to claim 12, wherein the passages have a substantially square cross-section.

14. The filter according to claim 1, wherein the passages have a combination of barrel-shaped cross-sections and trapezoidal cross-sections.

15. The filter according to claim 14, wherein a longer side of the trapezoidal passages is formed by the cover plate.

16. The filter according to claim 1, wherein the passages have an approximately square cross-section on the entry side of the filter that becomes wider towards the exit side of the filter.

17. The filter according to claim 1, wherein a spacing between the base plate in the area around the projections and the cover plate within a meandering row of projections is substantially constant.

18. The filter according to claim 5, wherein a spacing between the flat base plate in the area around the projections and the cover plate within a meandering row of projections linearly increases from the region of the end of the meandering row which is in the proximity of the inlet side of the filter in a direction towards the region of the end of the meandering row which is in the proximity of the outlet side of the filter.

19. A nebulizer for inhalation therapy, the nebulizer comprising a microstructured filter having an inlet for unfiltered fluid and an outlet for filtered fluid, the filter comprising:
a substantially flat base plate and a cover plate that is securable thereto,
a plurality of projections that each comprise an integral component of the base plate and which each project therefrom, the projections being spaced from one another by passages that form a fluid path through the filter from the inlet to the outlet, the cover plate when secured to the base plate covering the projections and the passages;
wherein the plurality of projections form at least one row which is arranged in a meander configuration in a mutually juxtaposed relationship across the filter; and
wherein the passages have a length of 5 µm to 50 µm, a height of 2.5 µm to 25 µm, and a width of 2.5 µm to 25 µm.

20. The nebulizer according to claim 19, comprising a nozzle in assembly with the filter.

* * * * *